(12) United States Patent
Berger et al.

(10) Patent No.: US 10,633,553 B2
(45) Date of Patent: Apr. 28, 2020

(54) ENERGY CURABLE HIGH REACTIVITY MULTI VINYLETHER OR ACRYLATE FUNCTIONAL RESINS

(71) Applicant: BASF SE, Ludwigshafen (DE)

(72) Inventors: Sebastian Berger, Ann Arbor, MI (US); Paul Share, Ann Arbor, MI (US)

(73) Assignee: BASF SE, Ludwigshafen (DE)

( * ) Notice: Subject to any disclaimer, the term of this patent is extended or adjusted under 35 U.S.C. 154(b) by 36 days.

(21) Appl. No.: 15/768,288

(22) PCT Filed: Sep. 23, 2016

(86) PCT No.: PCT/US2016/053469
§ 371 (c)(1),
(2) Date: Apr. 13, 2018

(87) PCT Pub. No.: WO2017/065957
PCT Pub. Date: Apr. 20, 2017

(65) Prior Publication Data
US 2018/0312715 A1    Nov. 1, 2018

Related U.S. Application Data

(60) Provisional application No. 62/242,837, filed on Oct. 16, 2015.

(51) Int. Cl.
| | | |
|---|---|---|
| C09D 135/08 | (2006.01) | |
| C09D 169/00 | (2006.01) | |
| C09D 11/101 | (2014.01) | |
| C09D 11/106 | (2014.01) | |
| C09D 11/107 | (2014.01) | |
| C09D 4/00 | (2006.01) | |
| C07C 217/08 | (2006.01) | |
| C07C 217/28 | (2006.01) | |
| C08F 26/02 | (2006.01) | |

(Continued)

(52) U.S. Cl.
CPC .......... *C09D 135/08* (2013.01); *C07C 217/08* (2013.01); *C07C 217/28* (2013.01); *C07C 323/12* (2013.01); *C08F 26/02* (2013.01); *C08G 64/025* (2013.01); *C08G 64/0241* (2013.01); *C08G 64/0291* (2013.01); *C08G 64/42* (2013.01); *C09D 4/00* (2013.01); *C09D 11/101* (2013.01); *C09D 11/106* (2013.01); *C09D 11/107* (2013.01); *C09D 135/02* (2013.01); *C09D 169/00* (2013.01); *C09J 4/00* (2013.01); *C09J 135/02* (2013.01); *C09J 135/08* (2013.01)

(58) Field of Classification Search
CPC .. C09D 135/08; C09D 11/107; C09D 11/106; C09J 135/08; C07C 217/28; C07C 323/12; C08G 64/0291; C08G 64/025; C08G 64/0241
See application file for complete search history.

(56) References Cited

U.S. PATENT DOCUMENTS

| 3,844,916 A | 10/1974 | Gaske |
| 3,963,771 A | 6/1976 | Robson et al. |

(Continued)

FOREIGN PATENT DOCUMENTS

| DE | 10138216 A1 | 2/2003 |
| DE | 10147712 A1 | 4/2003 |

(Continued)

OTHER PUBLICATIONS

U.S. Appl. No. 62/165,086, filed May 21, 2015, Share, et al.

(Continued)

*Primary Examiner* — Paul A Zucker
(74) *Attorney, Agent, or Firm* — Foley & Lardner LLP

(57) ABSTRACT

The present technology provides a heteroatom-containing polycarbonate polyfunctional-vinyl ether molecule of formula (I) and processes of preparing thereof. The present technology further provides a heteroatom-containing acrylate molecule of formula (II). An ink or coating formulation including an energy curable high reactivity heteroatom-containing polycarbonate polyfunctional-vinyl ether molecule of formula (I) or an energy curable high reactivity heteroatom-containing acrylate molecule of formula (II) is provided.

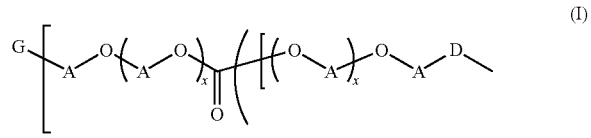

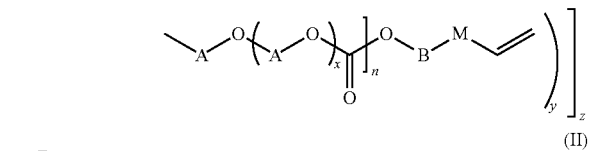

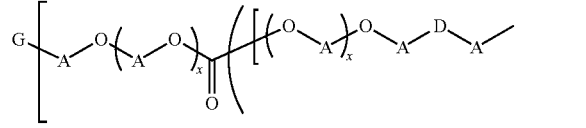

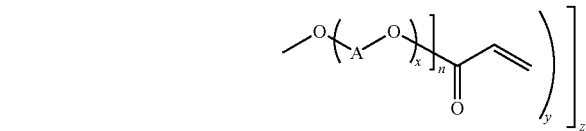

16 Claims, 1 Drawing Sheet

(51) Int. Cl.
  *C08G 64/02* (2006.01)
  *C08G 64/42* (2006.01)
  *C09J 4/00* (2006.01)
  *C09J 135/02* (2006.01)
  *C09J 135/08* (2006.01)
  *C07C 323/12* (2006.01)
  *C09D 135/02* (2006.01)

(56) References Cited

U.S. PATENT DOCUMENTS

| | | | |
|---|---|---|---|
| 5,159,098 A * | 10/1992 | Plotkin | C07C 271/12 522/170 |
| 5,180,424 A | 1/1993 | Hutter | |
| 6,172,129 B1 | 1/2001 | Fan et al. | |
| 8,952,190 B2 | 2/2015 | Davidson et al. | |
| 2015/0253466 A1 | 9/2015 | Ibuki et al. | |

FOREIGN PATENT DOCUMENTS

| | | |
|---|---|---|
| EP | 0 280 222 A2 | 8/1988 |
| EP | 0 297 344 A2 | 1/1989 |
| EP | 0 355 558 A1 | 2/1990 |
| EP | 1 616 922 A1 | 1/2006 |
| EP | 1 731 541 A1 | 12/2006 |
| EP | 1 876 166 A1 | 1/2008 |
| EP | 2 097 458 A1 | 9/2009 |
| EP | 2 121 771 A1 | 11/2009 |
| EP | 2 367 056 A2 | 9/2011 |
| WO | WO-91/13052 A1 | 9/1991 |
| WO | WO-02/22700 A2 | 3/2002 |
| WO | WO-02/32851 A1 | 4/2002 |
| WO | WO-2015/022511 A1 | 2/2015 |

OTHER PUBLICATIONS

International Search Report and Written Opinion in International Application No. PCT/US2016/053469 dated Jan. 26, 2017 (13 pages).

Otera, "Transesterification," Chemical Reviews, 1993, pp. 1449-1470, vol. 93, No. 4.

* cited by examiner

ENERGY CURABLE HIGH REACTIVITY MULTI VINYLETHER OR ACRYLATE FUNCTIONAL RESINS

CROSS-REFERENCE TO RELATED APPLICATIONS

The present application is a U.S. National Phase Application under 35 U.S.C. § 371 of International Application No. PCT/US2016/053469, filed on Sep. 23, 2016, which claims the benefit of U.S. Provisional Patent Application No. 62/242,837, filed on Oct. 16, 2015, and which are each incorporated herein by reference in their entireties.

FIELD

The present technology is generally related to energy curable high reactivity multi vinylether or acrylate functional resins, methods of their preparation through an azeotropic transesterification process, and their use in downstream applications.

BACKGROUND

There are several factors which are critical to the commercial success of UV (ultraviolet light) and EB (electron beam) curable coatings and inks. As printing presses and coater equipment run at higher and higher speeds, reducing the hourly cost of production, there are increasing demands on the curing speed of inks and coatings. At the same time, there is considerable focus by converters on energy consumption, such that there is a trend toward lower mercury lamp energies, and in many cases, conversion to LED light sources. Both higher line speeds and lower intensity light sources place demands on the reactivity of the monomers and oligomers used in formulations for such applications.

Another important factor for packaging applications is the increasing use of film substrates in bags, pouches, and labels. These substrates are very thin, but as a result, any shrinkage that occurs in the coating and ink during the curing process can result in wrinkling or other distortion of the film. Furthermore, in some cases, there is adhesion loss of the ink or coating to the film. Since these films are often used to package foods or beverages, there are very strict limits on the migration of unreacted monomers from the ink or coating.

SUMMARY

In one aspect, a heteroatom-containing polycarbonate polyfunctional-vinyl ether molecule of formula (I) is provided:

wherein
G is S or N;
each D is independently S, O, or $N^{R10}$, wherein $R^{10}$ has the structure:

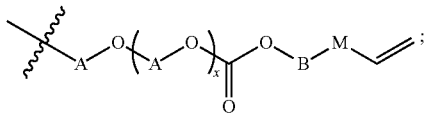

each A is independently a $C_1$-$C_{10}$ alkylene group;
each B is independently a $C_1$-$C_{10}$ alkylene group;
each M is independently O or S;
each x is independently an integer from 0 to 10;
each n is independently an integer from 0 to 20;
each y is independently an integer from 1 to 20; and
z is 2 when G is S or z is 3 when G is N.

In another aspect, a process is provided for preparing a heteroatom-containing polycarbonate polyfunctional-vinyl ether molecule of formula (I) as disclosed herein. The process includes contacting in a solvent a heteroatom-containing polyol with a carbonate in the presence of a catalyst to form a reaction mixture; heating the reaction mixture under azeotropic reflux conditions to form an alcohol or water and a heteroatom-containing polycarbonate; isolating the heteroatom-containing polycarbonate from the excess carbonate and solvent; contacting the isolated heteroatom-containing polycarbonate with a vinyl ether in the presence of a catalyst to form a second reaction mixture; and heating the reaction mixture under azeotropic reflux conditions to form a second alcohol or water. The reaction is pushed forward by the removal of the alcohols or water (produced as by-products) from the reaction mixture under azeotropic reflux conditions.

In one aspect, a process is provided for preparing a heteroatom-containing polycarbonate polyfunctional-vinyl ether molecule of formula (I) as disclosed herein. The process includes contacting in a solvent a hydroxy-functional vinyl ether with a carbonate in the presence of a catalyst to form a reaction mixture; heating the reaction mixture under azeotropic reflux conditions to form an alcohol or water and a vinyl ether carbonate; isolating the vinyl ether carbonate from the excess carbonate and solvent; contacting the isolated vinyl ether carbonate with a heteroatom-containing polyol in the presence of a catalyst to form a second reaction mixture; and heating the reaction mixture under azeotropic reflux conditions to form a second alcohol or water. The reaction is driven forward by the removal of the alcohols or water (produced as by-products) from the reaction mixture under azeotropic reflux conditions.

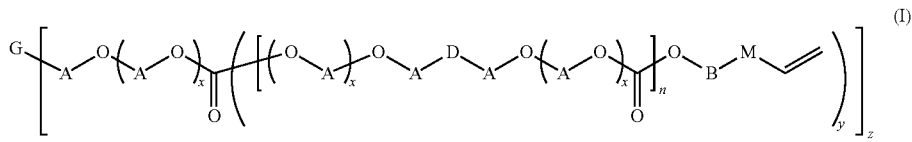

(I)

In another aspect, a heteroatom-containing acrylate molecule of formula (II) is provided:

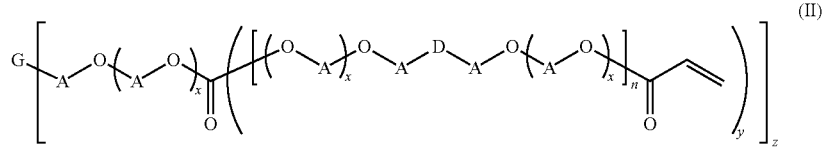

wherein
G is S or N;
each A is independently a $C_1$-$C_{10}$ alkylene group;
each D is independently S, O, or $N^{R^{10}}$, wherein $R^{10}$ has the structure:

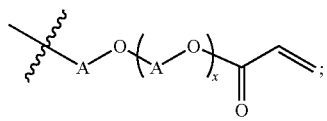

each x is independently an integer from 0 to 10;
each n is independently an integer from 0 to 20;
each y is independently an integer from 1 to 20; and
z is 2 when G is S or z is 3 when G is N.

In another aspect, a coating composition is provided. The coating composition includes a heteroatom-containing polycarbonate polyfunctional-vinyl ether molecule of formula (I) as disclosed herein or a heteroatom-containing acrylate molecule of formula (II) as disclosed herein.

In another aspect, an ink or coating formulation is provided. The ink or coating formulation includes a heteroatom-containing polycarbonate polyfunctional-vinyl ether molecule of formula (I) as disclosed herein or a heteroatom-containing acrylate molecule of formula (II) as disclosed herein.

In yet another aspect, an optical fiber coating is provided. The optical fiber coating includes a heteroatom-containing polycarbonate polyfunctional-vinyl ether molecule of formula (I) as disclosed herein or a heteroatom-containing acrylate molecule of formula (II) as disclosed herein.

DETAILED DESCRIPTION

Figure 1:
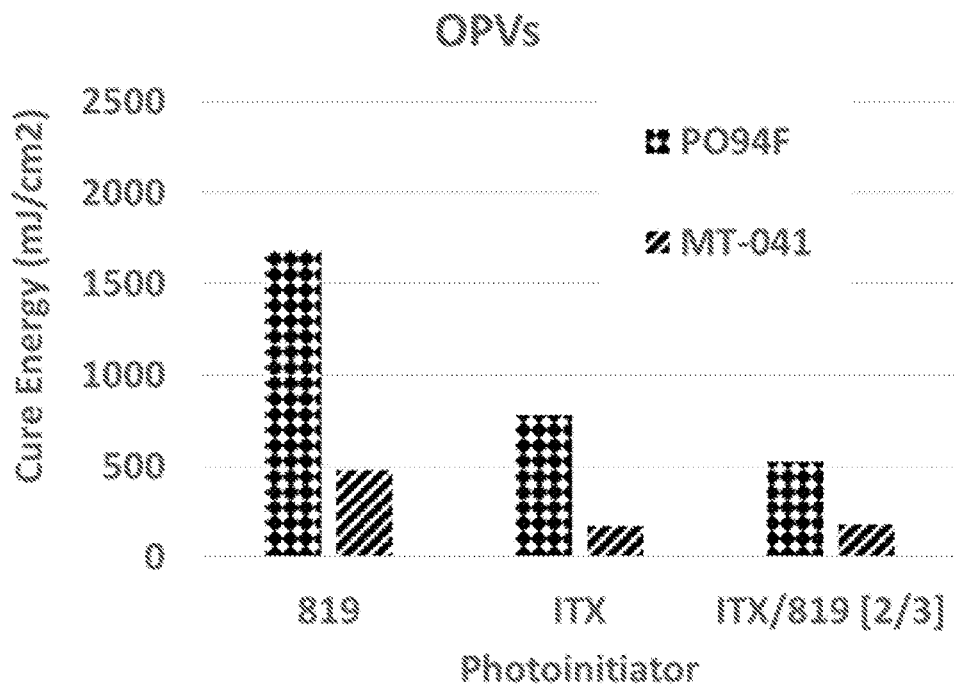
FIG. 1 is a chart illustrating the decreased cure energy (i.e., increased cure speed) of a triethanolamine-carbonate-vinyl ether adduct (MT-041) as compared to a conventional Michael adduct of an acrylate (Laromer® PO94F), according to the examples.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, the term "substituted," unless specifically defined differently, refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. For some groups, substituted may provide for attachment of an alkyl group to another defined group, such as a cycloalkyl group.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group. In general, alkyl groups may include in addition to those listed above, but are not limited to, 2-pentyl, 2-methylbutyl, 3-methylbutyl, 1,2-dimethylpropyl, 1,1-dimethylpropyl, 2,2-dimethylpropyl, 1-ethylpropyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, 2-heptyl, 3-heptyl, 2-ethylpentyl, 1-propylbutyl, 2-ethylhexyl, 2-propylheptyl, 1,1,3,3-tetramethylbutyl, nonyl, decyl, n-undecyl, n-dodecyl, n-tridecyl, iso-tridecyl, n-tetradecyl, n-hexadecyl, n-octadecyl, n-eicosyl, and the like.

Alkylene groups are divalent alkyl groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

As used herein, the term (meth)acrylic or (meth)acrylate refers to acrylic or methacrylic acid, esters of acrylic or methacrylic acid, and salts, amides, and other suitable derivatives of acrylic or methacrylic acid, and mixtures thereof. Illustrative examples of suitable (meth)acrylic monomers include, without limitation, the following methacrylate esters: methyl methacrylate, ethyl methacrylate, n-propyl methacrylate, n-butyl methacrylate (BMA), isopropyl methacrylate, isobutyl methacrylate, n-amyl methacrylate, n-hexyl methacrylate, isoamyl methacrylate, 2-hydroxyethyl methacrylate, 2-hydroxypropyl methacrylate, N,N-dimethylaminoethyl methacrylate, N,N-diethylaminoethyl methacrylate, t-butylaminoethyl methacrylate, 2-sulfoethyl methacrylate, trifluoroethyl methacrylate, glycidyl methacrylate (GMA), benzyl methacrylate, allyl methacrylate, 2-n-butoxyethyl methacrylate, 2-chloroethyl methacrylate, sec-butyl-methacrylate, tert-butyl methacrylate, 2-ethylbutyl methacrylate, cinnamyl methacrylate, crotyl methacrylate, cyclohexyl methacrylate, cyclopentyl methacrylate, 2-ethoxyethyl methacrylate, furfuryl methacrylate, hexafluoroisopropyl methacrylate, methallyl methacrylate, 3-methoxybutyl methacrylate, 2-methoxybutyl methacrylate, 2-nitro-2-methylpropyl methacrylate, n-octylmethacrylate, 2-ethylhexyl methacrylate, 2-phenoxyethyl methacrylate, 2-phenylethyl methacrylate, phenyl methacrylate, propargyl methacrylate, tetrahydrofurfuryl methacrylate and tetrahydropyranyl methacrylate. Example of suitable acrylate esters include, without limitation, methyl acrylate, ethyl acrylate, n-propyl acrylate, isopropyl acrylate, n-butyl acrylate (BA), n-decyl acrylate, isobutyl acrylate, n-amyl acrylate, n-hexyl acrylate, isoamyl acrylate, 2-hydroxyethyl acrylate, 2-hydroxypropyl acrylate, N,N-dimethylaminoethyl acrylate, N,N-diethylaminoethyl acrylate, t-butylaminoethyl acrylate, 2-sulfoethyl acrylate, trifluoroethyl acrylate, glycidyl acrylate, benzyl acrylate, allyl acrylate, 2-n-butoxyethyl acrylate, 2-chloroethyl acrylate, sec-butyl-acrylate, tert-butyl acrylate, 2-ethylbutyl acrylate, cinnamyl acrylate, crotyl acrylate, cyclohexyl acrylate, cyclopentyl acrylate, 2-ethoxyethyl acrylate, furfuryl acrylate, hexafluoroisopropyl acrylate, methallyl acrylate, 3-methoxybutyl acrylate, 2-methoxybutyl acrylate, 2-nitro-2-methylpropyl acrylate, n-octylacrylate, 2-ethylhexyl acrylate, 2-phenoxyethyl acrylate, 2-phenylethyl acrylate, phenyl acrylate, propargyl acrylate, tetrahydrofurfuryl acrylate and tetrahydropyranyl acrylate.

As used herein, the term "acrylic-containing group" or "methacrylate-containing group" refers to a compound that has a polymerizable acrylate or methacrylate group.

As noted above, there are very strict limits on the migration of unreacted monomers from curable inks or coatings, particularly when used in food packaging applications. The current state of the art addresses the reactivity issue by either maximizing the number of reactive acrylate double bonds per unit molecular weight and/or by introducing resins that increase the cure speed due to synergistic effects and reduced oxygen inhibition. Examples covering the latter approach are alkyl amine and thioether resins manufactured by post-modification of acrylate functional resins via amine- or thio-Michael additions at acrylic double bonds.

The effect of such molecules thereby is twofold. The combination of tertiary amines with photo-excited species such as benzophenone in a UV formulation leads to the formation of an α-methylene based radical which acts as a polymerization agent. This is referred to as an amine synergist. In addition, these α-methylene based radicals can also be formed by reaction with peroxy radical intermediates resulting from the reaction of atmospheric oxygen with acrylate radicals. These acrylate based peroxy radical intermediates would otherwise inhibit further acrylate polymerization in a coating or ink. The corresponding thioethers react in a similar fashion.

The state-of-the-art approach is advantageous due to relatively low resin manufacturing costs. While it is sufficient for some applications, it has certain disadvantages in others. One disadvantage is the loss of energy cure responsive double bond density due to the Michael addition of an amine, thiol or similar heteroatom component to an acrylate group of the precursor resin. The more mono or di-substituted amines are incorporated into the resin, the lower the acrylate functionality of the final resin and the higher the probability that non-UV active, migrating components are present, which is of great concern, especially in sensitive food packaging applications.

Additionally, in order to minimize the risk of reducing the average functionality per molecule, primary amines with two Michael-active amine protons are frequently used for functionalization purposes, which leads to a chain extension of the precursor resin. Since coatings and inks are generally formulated to a specific application viscosity, and higher molecular weight often increases viscosity, the flexibility in formulating coatings and inks containing these materials becomes limited. This is of particular concern in UV inkjet printing applications, which require very low application viscosities.

Another disadvantage pertains to the increased inhibitor levels required to ensure process and storage stability of the highly reactive Michael adducts. This ultimately decreases the cure speeds of the coating or ink on a coating or printing line.

It has now been surprisingly found that multifunctional vinyl ether functional polycarbonate heteroatom-containing straight and branched polycarbonates as described herein in various embodiments, have a significantly improved cure profile over products made according to the state-of-the-art process but lack any of the above mentioned disadvantages. Such polycarbonates include heteroatom-containing polycarbonate polyfunctional-vinyl ether molecules of formula (I) and straight and branched heteroatom-containing acrylate molecules of formula (II) as described herein in various embodiments. In one embodiment, the polycarbonates disclosed herein can be based on alkoxylated triethanolamine or thiodiglycol.

Provided herein are heteroatom-containing energy cure active molecules with polyol backbones, which are rendered energy cure active in a holistic approach. These heteroatom-containing energy cure active molecules with polyol backbones do not require post-functionalization via Michael addition reaction to obtain the desired α-methylene reactive center and thus lack the problems typically associated with Michael adducts.

The multifunctional vinyl ether functional polycarbonate heteroatom-containing straight and branched polycarbonates provided herein have a number of advantages compared to Michael adducts. The weight percent of nitrogen (or other heteroatoms) per unit weight is much higher than for Michael adducts, which results in a higher number of α-methylene reactive centers per unit weight. Additionally, the conversion of an energy-curable functional group to a Michael adduct generally reduces reactivity and crosslink density, which is not an issue for the molecules provided herein. Third, termination of the core molecule with vinyl ether groups rather than (meth)acrylic esters also removes the requirement for free radical inhibition during manufacturing and storage time, since vinyl ethers do not self-react under free radical conditions. Fourth, combining the terminal vinyl ether with the core carbonate structure significantly reduces the overall polarity of the molecule and its resulting viscosity in comparison to the more polar Michael adducts.

In one aspect, a heteroatom-containing polycarbonate polyfunctional-vinyl ether molecule of formula (I) is provided:

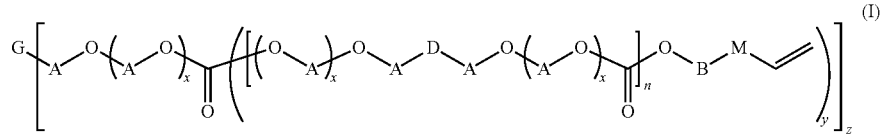

wherein

G is S or N;

each D is independently S, O, or $N^{R10}$, wherein $R^{10}$ has the structure:

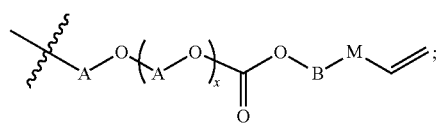

each A is independently a $C_1$-$C_{10}$ alkylene group;

each B is independently a $C_1$-$C_{10}$ alkylene group;

each M is independently O or S;

each x is independently an integer from 0 to 10;

each n is independently an integer from 0 to 20;

each y is independently an integer from 1 to 20; and z is 2 when G is S or z is 3 when G is N.

In one embodiment, each A independently is an optionally substituted $C_1$-$C_{10}$ alkylene group. In another embodiment, each A independently is —$CH_2CH_2$—.

In one embodiment, each B independently is a $C_1$-$C_{10}$ alkylene group optionally substituted with one or more $R^2$ groups, wherein each $R^2$ group independently is a $C_1$-$C_6$ alkyl or two $R^2$ groups can join together to form a 5, 6, or 7-membered cycloalkyl. In another embodiment, each B independently is:

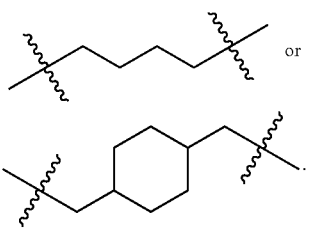

In one embodiment, the polyfunctional-vinyl ether molecule of formula (I) is selected from the group consisting of:

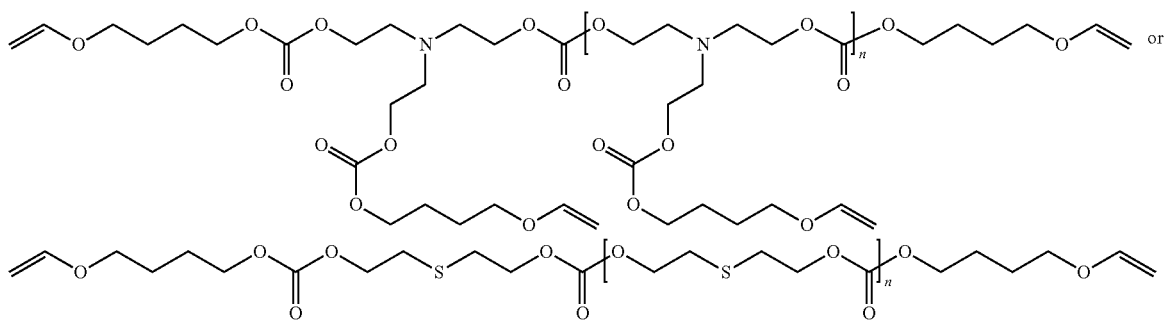

In one embodiment, the polyfunctional-vinyl ether molecules exhibits a viscosity from about 10 centipoise to about 1000 centipoise at 25° C. (when neat). In another embodiment, the polyfunctional-vinyl ether molecule provided herein exhibits a viscosity of about 10 centipoise to about 300 centipoise at 25° C.

In one aspect, a process is provided for preparing a heteroatom-containing polycarbonate polyfunctional-vinyl ether molecule of formula (I). The process includes contacting in a solvent a heteroatom-containing polyol with a carbonate in the presence of a catalyst to form a reaction mixture; heating the reaction mixture under azeotropic reflux conditions to form an alcohol or water and a heteroatom-containing polycarbonate; isolating the heteroatom-containing polycarbonate from the excess carbonate and solvent; contacting the isolated heteroatom-containing polycarbonate with a vinyl ether in the presence of a catalyst to form a second reaction mixture; and heating the reaction mixture under azeotropic reflux conditions to form a second alcohol or water. The reaction is driven forward by the removal of the alcohols or water (produced as by-products) from the reaction mixture under azeotropic reflux conditions.

In one embodiment, the heteroatom-containing polyol is an alkanolamine, a thioalcohol, an alkoxyamine, or a thioalkoxy. In another embodiment, the heteroatom-containing polyol is triethanolamine or thiodiglycol.

In one embodiment, the carbonate is an alkyl ester of an organic polyacid. In another embodiment, the carbonate is dimethyl carbonate, diethyl carbonate, dimethyl adipate, diethyl adipate, or citric acid triethyl ester.

The contacting of the heteroatom-containing polyol with the carbonate and the catalyst in a solvent may occur in different orderings. For example, the contacting of the heteroatom-containing polyol with the carbonate and the catalyst can occur simultaneously. Alternatively, the contacting of the heteroatom-containing polyol with the carbonate and the catalyst can occur sequentially wherein the order of addition varies. In some embodiments, the heteroatom-containing polyol is added to the solvent, followed by the addition of the carbonate, and subsequently the addition of the catalyst.

The heteroatom-containing polyol, carbonate, and catalyst are heated to achieve azeotropic reflux conditions to facilitate removal of an alcohol or water formed by the reaction. In one embodiment, the reaction mixture is heated to a temperature of about 70° C. to about 140° C. In another embodiment, the reaction mixture is heated to about 100° C. In some embodiments, the azeotropic mixture has a boiling point of about 54-55° C. The reaction is pushed forward by the removal of the alcohol or water by-product under the azeotropic reflux conditions.

The reaction of the heteroatom-containing polyol, carbonate, and catalyst produces a heteroatom-containing polycarbonate that is then isolated. The isolated heteroatom-containing polycarbonate is then contacted with a vinyl ether in the presence of a catalyst to form a second reaction mixture. In one embodiment, the vinyl ether is 4-hydroxybutyl vinyl ether, cyclohexanedimethanol mono-vinyl ether, or 2-vinylsulfanylethanol. These hydroxyl vinyl ethers and other similar hydroxyl vinyl ethers are commercially available. Additionally, preparations of the aforementioned hydroxyl vinyl ethers and other similar hydroxyl vinyl ethers are well known in the art. For example, an alcohol or mercaptoalcohol is heated under pressure in the presence of a strong base, like methoxide or hydroxide, in the presence of acetylene. The base-catalyzed condensation of acetylene with the alcohol occurs at about 120-180° C. The reaction proceeds by the formation of an alcoholate, which undergoes nucleophilic addition to the acetylenic double bond. The product regenerates the alcoholate by proton exchange.

The contacting of the heteroatom-containing polycarbonate with the vinyl ether and the catalyst in a solvent may occur in different orderings. For example, the contacting of the heteroatom-containing polycarbonate with the vinyl ether and the catalyst can occur simultaneously. Alternatively, the contacting of the heteroatom-containing polycarbonate with the vinyl ether and the catalyst can occur sequentially wherein the order of addition varies. In some embodiments, the heteroatom-containing polycarbonate is added to the solvent, followed by the addition of the vinyl ether, and subsequently the addition of the catalyst.

The heteroatom-containing polycarbonate, vinyl ether, and catalyst are heated to achieve azeotropic reflux conditions to facilitate removal of an alcohol or water formed by the reaction. In one embodiment, the reaction mixture is heated to a temperature of about 70° C. to about 140° C. This may include heating the reaction mixture from about 70° C. to about 120° C., from about 80° C. to about 140° C., from about 90° C. to about 110° C. In another embodiment, the reaction mixture is heated to about 100° C. In some embodiments, the azeotropic mixture has a boiling point of about 54° C. to about 55° C. The reaction is driven forward by the removal of the alcohol or water by-product under the azeotropic reflux conditions.

The catalyst used for the process disclosed herein includes any catalyst that is capable of catalyzing a transesterification reaction which includes all catalysts listed in Otera, *Chem. Rev.* 1993, 93, 1449-1470. Illustrative catalysts include, but are not limited to, alkali metal hydroxides, alkali metal carbonates, alkali metal hydrogen carbonates, preferably of sodium, of potassium or of cesium, tertiary amines, guanidines, ammonium compounds, phosphonium compounds, organoaluminum, organotin, organozinc, organotitanium, organozirconium or organobismuth compounds, and double metal cyanide (DMC) catalysts, as described, for example, in DE 10138216 and in DE 10147712, both of which are hereby incorporated by reference in their entireties. In some embodiments, the catalyst is a strong base, a mild transesterification catalyst, or a Lewis acid.

Specific examples of catalysts include, but are not limited to, potassium hydroxide, potassium carbonate, potassium hydrogen carbonate, diazabicyclooctane (DABCO), diazabicyclononene (DBN), diazabicycloundecene (DBU), imidazoles, such as imidazole, 1-methylimidazole or 1,2-dimethylimidazole, titanium tetrabutoxide, titanium tetraisopropoxide, dibutyltin oxide, dibutyltin dilaurate, tin dioctoate, zirconium acetylacetonate, or mixtures of any two or more thereof. In some embodiments, the catalyst is potassium hydroxide, sodium hydroxide, and sodium methoxide. Mixtures of any two or more such catalysts may be employed.

The solvent of the disclosed process may be any solvent that can function as an azeotropic solvent. An azeotropic solvent is a solvent that forms an azeotrope with another material such as an alcohol or water. Examples of azeotropic solvents include, but are not limited to $C_5$-$C_{10}$ alkanes, $C_5$-$C_{10}$ cycloalkanes, and aromatic solvents. In some embodiments, the azeotropic solvent is cyclohexane, toluene, dimethyl carbonate, or heptane. Mixtures of any two or more such solvents may be employed.

In another aspect, a process is provided for preparing a heteroatom-containing polycarbonate polyfunctional-vinyl ether molecule of formula (I) as disclosed herein. The process includes contacting in a solvent a hydroxy-functional vinyl ether with a carbonate in the presence of a catalyst to form a reaction mixture; heating the reaction mixture under azeotropic reflux conditions to form an alcohol or water and a vinyl ether carbonate; isolating the vinyl ether carbonate from the excess carbonate and solvent; contacting the isolated vinyl ether carbonate with a heteroatom-containing polyol in the presence of a catalyst to form a second reaction mixture; and heating the reaction mixture under azeotropic reflux conditions to form a second alcohol or water. The reaction is pushed forward by the removal of the alcohols or water (produced as by-products) from the reaction mixture under azeotropic reflux conditions.

In one embodiment, the hydroxy-functional vinyl ether is 4-hydroxybutyl vinyl ether, cyclohexanedimethanol monovinyl ether, or 2-vinylsulfanylethanol.

In one embodiment, the carbonate is an alkyl ester of an organic polyacid. In another embodiment, the carbonate is dimethyl carbonate, diethyl carbonate, dimethyl adipate, diethyl adipate, or citric acid triethyl ester.

The contacting of the hydroxy-functional vinyl ether with the carbonate and the catalyst in a solvent may occur in different orderings. For example, the contacting of the hydroxy-functional vinyl ether with the carbonate and the catalyst can occur simultaneously. Alternatively, the contacting of the hydroxy-vinyl ether with the carbonate and the catalyst can occur sequentially wherein the order of addition varies. In some embodiments, the hydroxy-functional vinyl ether is added to the solvent, followed by the addition of the carbonate, and subsequently the addition of the catalyst.

The hydroxy-functional vinyl ether, carbonate, and catalyst are heated to achieve azeotropic reflux conditions to facilitate removal of an alcohol or water formed by the reaction. In one embodiment, the reaction mixture is heated to a temperature of about 70° C. to about 140° C. In another embodiment, the reaction mixture is heated to about 100° C. In some embodiments, the azeotropic mixture has a boiling point of about 54-55° C. The reaction is pushed forward by the removal of the alcohol or water by-product under the azeotropic reflux conditions.

The reaction of the hydroxy-functional vinyl ether, carbonate, and catalyst produces a vinyl ether carbonate, which is then isolated. The isolated vinyl ether carbonate is then contacted with a heteroatom-containing polyol in the presence of a catalyst to form a second reaction mixture.

In one embodiment, the heteroatom-containing polyol is an alkanolamine, a thioalcohol, an alkoxyamine, or a thioalkoxy. In another embodiment, the heteroatom-containing polyol is triethanolamine or thiodiglycol.

The contacting of the heteroatom-containing polyol with the vinyl ether carbonate and the catalyst in a solvent may occur in different orderings. For example, the contacting of the heteroatom-containing polyol with the vinyl ether carbonate and the catalyst can occur simultaneously. Alternatively, the contacting of the heteroatom-containing polyol with the vinyl ether carbonate and the catalyst can occur sequentially wherein the order of addition varies. In some embodiments, the heteroatom-containing polyol is added to the solvent, followed by the addition of the vinyl ether carbonate, and subsequently the addition of the catalyst.

The heteroatom-containing polyol, vinyl ether carbonate, and catalyst are heated to achieve azeotropic reflux conditions to facilitate removal of an alcohol or water formed by the reaction. In one embodiment, the reaction mixture is heated to a temperature of about 70° C. to about 140° C. This may include heating the reaction mixture from about 70° C. to about 120° C., from about 80° C. to about 140° C., from about 90° C. to about 110° C. In another embodiment, the reaction mixture is heated to about 100° C. In some embodiments, the azeotropic mixture has a boiling point of about 54° C. to about 55° C. The reaction is driven forward by the removal of the alcohol or water by-product under the azeotropic reflux conditions.

The catalyst used for the process disclosed herein includes any catalyst that is capable of catalyzing a transesterification reaction which includes all catalysts listed in Otera, *Chem. Rev.* 1993, 93, 1449-1470. Illustrative catalysts include but are not limited to, alkali metal hydroxides, alkali metal carbonates, alkali metal hydrogen carbonates, preferably of sodium, of potassium or of cesium, tertiary amines, guanidines, ammonium compounds, phosphonium compounds, organoaluminum, organotin, organozinc, organotitanium, organozirconium or organobismuth compounds, and also catalysts of the kind known as double metal cyanide (DMC) catalysts, as described, for example, in DE 10138216 and in DE 10147712, both of which are hereby incorporated by reference in their entireties. In some embodiments, the catalyst is a strong base, a mild transesterification catalyst, or a Lewis acid.

Specific examples of catalysts include but are not limited to potassium hydroxide, potassium carbonate, potassium hydrogen carbonate, diazabicyclooctane (DABCO), diazabicyclononene (DBN), diazabicycloundecene (DBU), imidazoles, such as imidazole, 1-methylimidazole or 1,2-dimethylimidazole, titanium tetrabutoxide, titanium tetraisopropoxide, dibutyltin oxide, dibutyltin dilaurate, tin dioctoate, zirconium acetylacetonate, or mixtures of any two or more thereof. In some embodiments, the catalyst is potassium hydroxide, sodium hydroxide, or sodium methoxide. Mixtures of any two or more such catalysts may be employed.

The solvent of the disclosed process can be any solvent that can function as an azeotropic solvent. An azeotropic solvent is a solvent that forms an azeotrope with another material such as an alcohol or water. Examples of an azeotropic solvent include but are not limited to $C_5$-$C_{10}$ alkane, a $C_5$-$C_{10}$ cycloalkane, or an aromatic solvent. In some embodiments, the solvent is cyclohexane, toluene, dimethyl carbonate, or heptane.

It has also been surprisingly found that acrylated heteroatom-based straight and branched polycarbonates, as described herein in various embodiments, also exhibit significantly improved cure profiles over products made according to the state of the art processes, but which lack the above-mentioned disadvantages of the Michael adducts. These acrylated heteroatom-based straight and branched polycarbonates include the heteroatom-containing acrylate molecule of formula (II) as disclosed herein. The heteroatom-containing alcohols are acrylated via a transesterification reaction of said alcohol with methyl acrylate to form the corresponding acrylic ester by removing the methanol by-product. The acrylated alcohols have to be inhibited against homopolymerization with radical inhibitors for their manufacturing and for storage stability reasons.

Despite their strong inhibition, these resins also show cure enhancement upon polymerizing them in standard energy cure formulations. The advantages over this system is again the uninfluenced functionality of the final acrylate, because the hetero atom (i.e. amine) is part of the molecular backbone rather than an amine-Michael addition product. The corresponding product viscosity at comparable molecular weight is slightly higher than the one of the vinylether version. Another advantage of this route are the manufacturing costs, which are lower than those of the vinylether resins, mostly due to raw material choice. However, a distinct disadvantage of the acrylic esters is their heavy radical inhibition, which can cause discoloration and adds low molecular weight species to the final resin. Nonetheless, the heteroatom-containing acrylates exhibit significantly increased cure speed when compared to state-of-the-art amine Michael-adducts.

In one aspect, a heteroatom-containing acrylate molecule of formula (II) is provided:

In one embodiment, each A independently is an optionally substituted $C_1$-$C_{10}$ alkylene group. In another embodiment, each A independently is —$CH_2CH_2$—.

In one embodiment, the acrylate molecule of formula (II) is selected from the group consisting of:

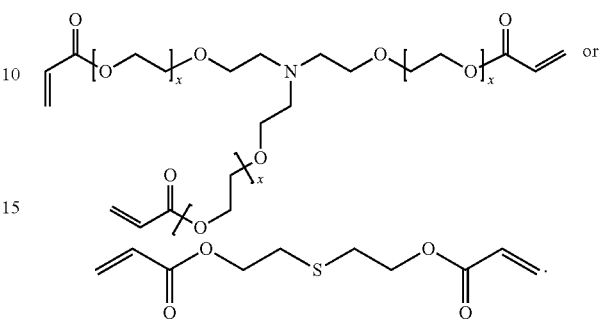

In one embodiment, the acrylate molecule of formula (II) exhibits a viscosity from about 10 centipoise to about 15000 centipoise at 25° C. In another embodiment, the acrylate molecule of formula (II) exhibits a viscosity of about 10 centipoise to about 1000 centipoise at 25° C.

The acrylate molecule of formula (II) can be prepared by a process as disclosed in U.S. Provisional Application No. 62/165,086. The process includes contacting in a solvent a heteroatom-containing polyol with an acrylate in the presence of a catalyst to form a reaction mixture and heating the reaction mixture under azeotropic reflux conditions to form an alcohol or water from the reaction mixture. The reaction is pushed forward by the removal of the alcohol or water (produced as by-products) from the reaction mixture under azeotropic reflux conditions.

The acrylate of the process disclosed above may be a (meth)acrylate. The (meth)acrylate may be acrylic acid, methacrylic acid, methylmethacrylic acid, methylmethacrylate, ethylmethacrylate, and hydroxy vinyl ethers. Other

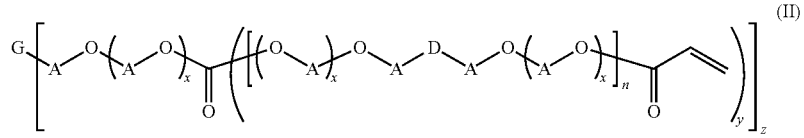

(II)

wherein

G is S or N;

each A is independently a $C_1$-$C_{10}$ alkylene group;

each D is independently S, O, or $N^{R10}$, wherein $R^{10}$ has the structure:

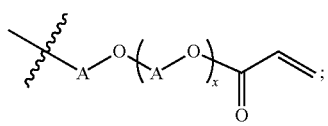

each x is independently an integer from 0 to 10;

each n is independently an integer from 0 to 20;

each y is independently an integer from 1 to 20; and z is 2 when G is S or z is 3 when G is N.

suitable examples of the (meth)acrylic or (meth)acrylate include, but are not limited to, methyl acrylate, ethyl acrylate, n-propyl acrylate, isopropyl acrylate, n-butyl acrylate (BA), n-decyl acrylate, isobutyl acrylate, n-amyl acrylate, n-hexyl acrylate, isoamyl acrylate, 2-hydroxyethyl acrylate, 2-hydroxypropyl acrylate, N,N-dimethylaminoethyl acrylate, N,N-diethylaminoethyl acrylate, t-butylaminoethyl acrylate, 2-sulfoethyl acrylate, trifluoroethyl acrylate, glycidyl acrylate, benzyl acrylate, allyl acrylate, 2-n-butoxyethyl acrylate, 2-chloroethyl acrylate, sec-butyl-acrylate, tert-butyl acrylate, 2-ethylbutyl acrylate, cinnamyl acrylate, crotyl acrylate, cyclohexyl acrylate, cyclopentyl acrylate, 2-ethoxyethyl acrylate, furfuryl acrylate, hexafluoroisopropyl acrylate, methallyl acrylate, 3-methoxybutyl acrylate, 2-methoxybutyl acrylate, 2-nitro-2-methylpropyl acrylate, n-octylacrylate, 2-ethylhexyl acrylate, 2-phenoxyethyl acrylate, 2-phenylethyl acrylate, phenyl acrylate, propargyl acrylate, tetrahydrofurfuryl acrylate and tetrahydropyranyl acrylate, methyl methacrylate, ethyl methacrylate, n-propyl methacrylate, n-butyl methacrylate (BMA), isopropyl methacrylate, isobutyl methacrylate, n-amyl methacrylate, n-hexyl methacrylate, isoamyl methacrylate, 2-hydroxyethyl methacrylate, 2-hydroxypropyl methacrylate, N,N-dimethylaminoethyl methacrylate, N,N-diethylaminoethyl methacrylate, t-butylaminoethyl methacrylate, 2-sulfoethyl methacrylate, trifluoroethyl methacrylate, glycidyl methacrylate (GMA), benzyl methacrylate, allyl methacrylate, 2-n-butoxyethyl methacrylate, 2-chloroethyl methacrylate, sec-butyl-methacrylate, tert-butyl methacrylate, 2-ethylbutyl methacrylate, cinnamyl methacrylate, crotyl methacrylate, cyclohexyl methacrylate, cyclopentyl methacrylate, 2-ethoxyethyl methacrylate, furfuryl methacrylate, hexafluoroisopropyl methacrylate, methallyl methacrylate, 3-methoxybutyl methacrylate, 2-methoxybutyl methacrylate, 2-nitro-2-methylpropyl methacrylate, n-octylmethacrylate, 2-ethylhexyl methacrylate, 2-phenoxyethyl methacrylate, 2-phenylethyl methacrylate, phenyl methacrylate, propargyl methacrylate, tetrahydrofurfuryl methacrylate and tetrahydropyranyl methacrylate. Examples of other suitable acrylic and methacrylic moieties include, but are not limited to hydroxyalkyl acrylates and methacrylates, acrylic acid and its salts, acrylonitrile, acrylamide, methyl α-chloroacrylate, methyl 2-cyanoacrylate, N-ethylacrylamide, N,N-diethylacrylamide, acrolein, methacrylic acid and its salts, methacrylonitrile, methacrylamide, N-methylmethacrylamide, N-ethylmethacrylamide, N,N-diethylmethacrylamide, N,N-dimethylmethacrylamide, N-phenylmethacrylamide, methacrolein and acrylic or methacrylic acid derivatives containing cross-linkable functional groups, such as hydroxy, carboxyl, amino, isocyanate, glycidyl, epoxy, allyl, and the like.

The catalyst employed in the process includes a catalyst that is capable of catalyzing transesterification reactions. Illustrative examples include the catalysts listed in Otera, *Chem. Rev.* 1993, 93, 1449-1470. Some examples of catalysts include but are not limited to, alkali metal hydroxides, alkali metal carbonates, alkali metal hydrogen carbonates, preferably of sodium, of potassium or of cesium, tertiary amines, guanidines, ammonium compounds, phosphonium compounds, organoaluminum, organotin, organozinc, organotitanium, organozirconium or organobismuth compounds, and also catalysts of the kind known as double metal cyanide (DMC) catalysts, as described, for example, in DE 10138216 or in DE 10147712. In some embodiments, the catalyst is a strong acid, a strong base, a transesterification catalyst, a Lewis acid, a Brønsted acid, or an amine. In other embodiments, the catalyst is an alkali alkoxide. In specific embodiments, the alkali alkoxide includes zinc isopropoxide, copper isopropoxide, zirconium acetoacetonate, or titanium tetra-isopropoxide.

Specific examples of catalysts include but are not limited to potassium hydroxide, potassium carbonate, potassium hydrogen carbonate, diazabicyclooctane (DABCO), diazabicyclononene (DBN), diazabicycloundecene (DBU), imidazoles, such as imidazole, 1-methylimidazole or 1,2-dimethylimidazole, titanium tetrabutoxide, titanium tetraisopropoxide, dibutyltin oxide, dibutyltin dilaurate, tin dioctoate, zirconium acetylacetonate, or mixtures thereof. In some embodiments, the catalyst is methane sulfonic acid, titanium isopropoxide, or an organotin reagent. In one embodiment, the organotin reagent is generated in situ through the reaction of sodium methoxide and dimethyltin dichloride.

The amount of catalyst present in the disclosed process is from about 400 ppm to about 1000 ppm based on one part of the heteroatom-containing polyol (based on weight of the monomers (heteroatom-containing polyol and acrylate) without solvent). In some embodiments, the amount of catalyst is about 1000 ppm based on one part of heteroatom-containing polyol (based on weight of the monomers (heteroatom-containing polyol and acrylate) without solvent).

The contacting of the heteroatom-containing polyol with the acrylate and catalyst in a solvent may occur in different orderings. For example, the contacting of the heteroatom-containing polyol with the acrylate and the catalyst may occur simultaneously. Alternatively, contacting of the heteroatom-containing polyol with the acrylate and catalyst may occur sequentially, wherein the order of addition varies. In some embodiments, the heteroatom-containing polyol is added to the solvent, followed by the addition of the catalyst, and subsequently the addition of the acrylate.

The solvent of the disclosed process may be any solvent that can function as an azeotropic solvent. An azeotropic solvent is a solvent that forms an azeotrope with another material such as an alcohol or water. Examples of azeotropic solvents include but are not limited to $C_5$-$C_{10}$ alkanes, $C_5$-$C_{10}$ cycloalkane, and $C_6$-$C_{12}$ aromatic solvents. In some embodiments, the solvent is pentane, hexane, heptane, octane, nonane, decane, cyclohexane, methyl cyclohexane, or toluene.

Once the heteroatom-containing polyol and acrylate are contacted with a catalyst in a solvent, the reaction mixture is heated to achieve azeotropic reflux conditions. In one embodiment, the reaction mixture is heated to about 70° C. to about 140° C. In another embodiment, the overhead temperature of the reaction has an azeotropic distillation temperature from about 40° C. to about 80° C. In some embodiments, the overhead temperature has an azeotropic distillation temperature of about 54° C. The reaction is pushed forward by the removal of the alcohol or water, produced as a by-product, under the azeotropic reflux conditions.

In another aspect, a coating composition is provided. The coating composition includes a heteroatom-containing polycarbonate polyfunctional-vinyl ether molecule of formula (I) as disclosed herein or a heteroatom-containing acrylate molecule of formula (II) as disclosed herein.

In another aspect, a coating, ink, or adhesive composition is provided. The coating, ink, or adhesive composition includes a heteroatom-containing polycarbonate polyfunctional-vinyl ether molecule of formula (I) as disclosed herein or a heteroatom-containing acrylate molecule of formula (II) as disclosed herein.

In one embodiment, the coating, ink, or adhesive composition is configured for use in conventional printing, 3D printing, inks, inkjet inks, paints, and packaging applications. In another embodiment, the coating, ink, or adhesive composition is configured for use in digital printing. In another embodiment, the coating, ink, or adhesive composition is configured for use in automotive original equipment manufacturer paint applications or automotive refinishing applications.

In yet another aspect, an optical fiber coating is provided. The optical fiber coating includes a heteroatom-containing polycarbonate polyfunctional-vinyl ether molecule of formula (I) as disclosed herein or a heteroatom-containing acrylate molecule of formula (II) as disclosed herein.

The present embodiments, thus generally described, will be understood more readily by reference to the following examples, which are provided by way of illustration and are not intended to be limiting of the present technology in any way.

EXAMPLES

Example 1. Synthesis of Compound 1

865 g triethanol amine, 3135 g dimethyl carbonate and 16 g of a 25 wt % sodium methoxide solution in methanol were heated and held at reflux for 30 min. The transesterification reaction started and methanol was generated and distilled off as an azeotropic mixture with dimethyl carbonate. Once the conversion reached the specification, the residual solvent was removed under reduced pressure at a maximum of 120° C. To this methyl carbonate function triethanol amine precursor, equimolar amounts of 4-hydroxybutyl vinyl ether (calculated on the concentration of methyl carbonate endgroups) and cyclohexane were charged at 60° C. The mixture was heated again to full reflux and as methanol was generated in this transesterification process, cyclohexane formed a low boiling azeotropic mixture with methanol, which was removed via an automated overhead reflux splitting mechanism. After reaching the desired high conversion, the product was purified via vacuum distillation under reduced pressure and temperatures at a maximum of 120° C. The final product exhibited a low viscosity and was a slightly brown free flowing resin.

Example 2. Synthesis of Compound 2

394 g thiodiglycol, 306 g dimethyl carbonate, 600 g cyclohexane and 3 g of a 25 wt % sodium methoxide solution in methanol were heated and held at reflux for 30 min. The transesterification reaction started and methanol was generated and distilled off as azeotropic mixture with cyclohexane overhead. Once the conversion reached the specification, the residual solvent was removed under reduced pressure at a maximum of 120° C. To this methyl carbonate functional thioether precursor, equimolar amounts of 4-hydroxybutyl vinyl ether (calculated on the concentration of methyl carbonate endgroups, determined by $^1$H-NMR) and 500 g cyclohexane were charged at 60° C. The mixture was heated again to full reflux and as methanol was generated in this transesterification process, cyclohexane formed a low boiling azeotropic mixture with methanol, which was removed via an automated overhead reflux splitting mechanism. After reaching the desired high conversion, the product was purified via vacuum distillation under reduced pressure and temperatures at a maximum of 120° C. The final product was a low viscosity, colorless free flowing resin.

Example 3. Synthesis of Compound 3

304 g triethanol amine polymer was homogenized with polymerization inhibitors (0.7 g mequinol, 2.3 g hydroquinone), 500 g cyclohexane and 405 g methyl acrylate. To this mixture, 13.6 g sodium methoxide 25% solution in methanol and 19.8 g dimethyltin dichloride 70% solution in methanol were charged. The mixture was heated under azeotropic conditions and methanol/cyclohexane azeotrope was removed from the reactor via an automated overhead reflux splitting mechanism. Once the reaction reached the desired conversion, the access monomer and solvent were removed via a vacuum distillation step. The catalyst was removed via a caustic wash and subsequent buffer wash of the diluted crude product. The final resin was obtained by vacuum distillation under reduced pressure and a maximum temperature of 100° C. The final product was a low viscosity, slightly brown resin.

Example 4. Synthesis of Compound 4

209 g thiodiglycol was homogenized with polymerization inhibitors (0.7 g mequinol, 2.3 g hydroquinone), 500 g cyclohexane and 441 g methyl acrylate. To this mixture, 13.6 g sodium methoxide 25% solution in methanol and 19.8 g dimethyltin dichloride 70% solution in methanol were charged. The mixture was heated under azeotropic conditions and methanol/cyclohexane azeotrope was removed from the reactor via an automated overhead reflux splitting mechanism. Once the reaction reached the desired conversion, the access monomer and solvent were removed via a vacuum distillation step. The catalyst was removed via a caustic wash and subsequent buffer wash of the diluted crude product. The final resin was obtained by vacuum distillation under reduced pressure and a maximum temperature of 100° C. The final product was a low viscosity, colorless resin.

Example 5

The cure energies of a triethanolamine-carbonate-vinyl ether adduct (MT041) was compared to that of an acrylic ester resin that is a conventional Michael adduct of an acrylate (PO94F) (see FIG. 1). FIG. 1 shows that the combination of a vinylether functionality with active alpha methylene groups on the same molecule results in increased cure speed, as demonstrated by the lower cure energy of MT041 than that of PO94F.

Figure 2:
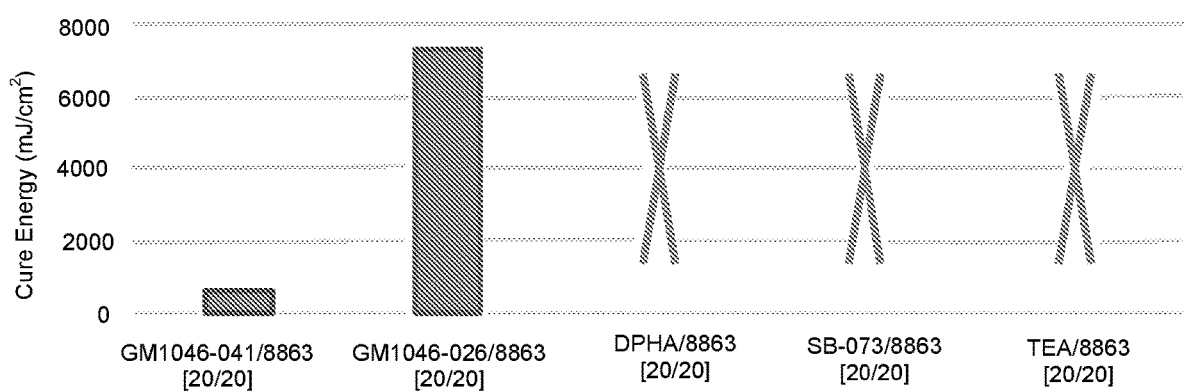
FIG. 2 is a chart illustrating the decreased cure energy (i.e., increased cure speed) of a triethanolamine-carbonate-vinyl ether adduct (GM1046-041/8863) as compared to a conventional vinyl ether (GM1046-026/8863) and triethanolamine (TEA/8863), according to the examples.

Example 6. The cure energies of a triethanolamine-carbonate-vinyl ether adduct (GM1046-041/8863) was compared to that of a vinyl ether (GM1046-026/8863) and triethanolamine (TEA/8863) (see FIG. 2). FIG. 2 shows that the vinyl ethers or amines alone do not improve cure properties in the same way as the combination of the two functionalities, as evidenced by the lower cure energy of GM1046-041/8863 as compared to that of GM1046-026/8863 and TEA/8863.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

The invention claimed is:

1. A polyfunctional-vinyl ether molecule of formula (I):

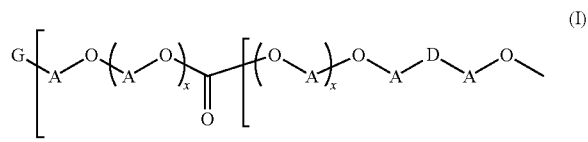
(I)

-continued

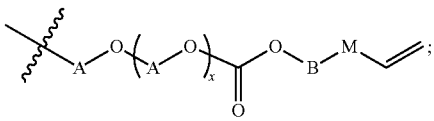

wherein
G is S or N;
each D is independently S, O, or $NR^{10}$, wherein $R^{10}$ has the structure:

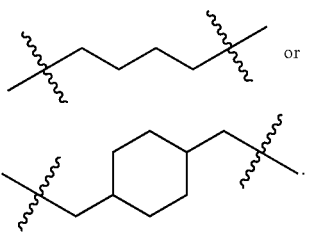

each A is independently a $C_1$-$C_{10}$ alkylene group;
each B is independently a $C_1$-$C_{10}$ alkylene group;
each M is independently O or S;
each x is independently an integer from 0 to 10;
each n is independently an integer from 0 to 20; and
z is 2 when G is S or z is 3 when G is N.

2. The polyfunctional-vinyl ether molecule of claim 1, wherein B is a $C_1$-$C_{10}$ alkylene group substituted with one or more $R^2$ groups, wherein each $R^2$ group independently is a $C_1$-$C_6$ alkyl or two $R^2$ groups can join together to form a 5, 6, or 7-membered cycloalkyl.

3. The polyfunctional-vinyl ether molecule of claim 1, wherein A is —$CH_2CH_2$.

4. The polyfunctional-vinyl ether molecule of claim 1, wherein B is selected from the group consisting of:

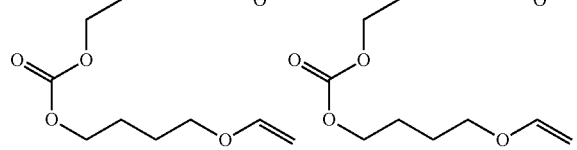

5. The polyfunctional-vinyl ether molecule of claim 1 selected from the group consisting of:

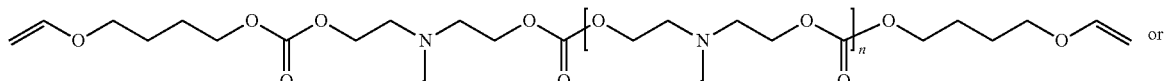

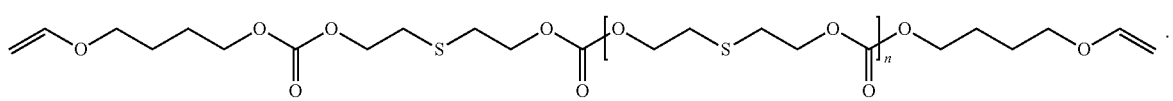

6. The polyfunctional-vinyl ether molecule of claim 1, wherein the molecule exhibits a viscosity from about 10 centipoise to about 1000 centipoise at 25° C.

7. A process of preparing a polyfunctional-vinyl ether molecule, the process comprising:
contacting in a solvent a heteroatom-containing polyol with a stoichiometric excess of carbonate in the presence of a catalyst to form a reaction mixture;
heating the reaction mixture under azeotropic reflux conditions to form a first alcohol or water and a heteroatom-containing polycarbonate;
isolating the heteroatom-containing polycarbonate from the excess carbonate and solvent;
contacting the isolated heteroatom-containing polycarbonate with a vinyl ether in the presence of a catalyst to form a second reaction mixture; and
heating the second reaction mixture under azeotropic reflux conditions to form a second alcohol or water; wherein:
the first alcohol, the second alcohol, and/or the water is removed from the reaction mixture or second reaction mixture under the azeotropic reflux conditions; and
the polyfunctional-vinyl ether molecule is a molecule of formula (I):

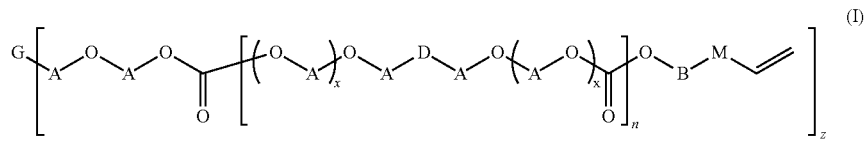

wherein
G is S or N;
each D is independently S, O, or $NR^{10}$, wherein $R^{10}$ has the structure:

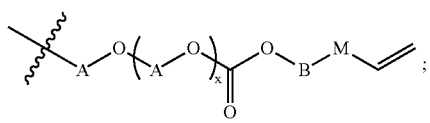

each A is independently a $C_1$-$C_{10}$ alkylene group;
each B is independently a $C_1$-$C_{10}$ alkylene group;
each M is independently O or S;
each x is independently an integer from 0 to 10;
each n is independently an integer from 0 to 20; and
z is 2 when G is S or z is 3 when G is N.

8. The process of claim 7, wherein the polyfunctional-vinyl ether molecule is prepared by a process comprising:
contacting in a solvent a hydroxyl-functional vinyl ether with a stoichiometric excess of carbonate in the presence of a catalyst to form a reaction mixture;
heating the reaction mixture under azeotropic reflux conditions to form a first alcohol or water and a vinyl ether carbonate; and
isolating the vinyl ether carbonate from the excess carbonate and solvent.

9. The process of claim 7, wherein heating the reaction mixture and heating the second reaction mixture comprises heating to a temperature of about 70° C. to about 140° C.

10. The process of claim 7, wherein the heteroatom-containing polyol comprises an alkanolamine, a thioalcohol, an alkoxyamine, or a thioalkoxy.

11. The process of claim 7, wherein the carbonate comprises an alkyl ester of an organic polyacid.

12. The process of claim 7, wherein the vinyl ether comprises 4-hydroxybutyl vinyl ether, cyclohexanedimethanol mono-vinyl ether, or 2-vinylsulfanylethanol.

13. The process of claim 7, wherein the catalyst comprises a strong base, a transesterification catalyst, or a Lewis acid.

14. The process of claim 7, wherein the solvent comprises $C_5$-$C_{10}$ alkane, $C_5$-$C_{10}$ cycloalkane, or an aromatic solvent.

15. An ink, coating, or adhesive composition comprising the polyfunctional-vinyl ether molecule of formula (I):

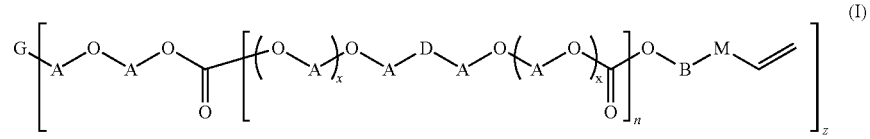

wherein
G is S or N;
each D is independently S, O, or $NR^{10}$, wherein $R^{10}$ has the structure:

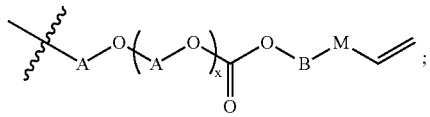

each A is independently a $C_1$-$C_{10}$ alkylene group;
each B is independently a $C_1$-$C_{10}$ alkylene group;
each M is independently O or S;
each x is independently an integer from 0 to 10;
each n is independently an integer from 0 to 20; and
z is 2 when G is S or z is 3 when G is N.

16. The process of claim 7, wherein the catalyst comprises sodium hydroxide, sodium methoxide, potassium hydroxide, potassium carbonate, potassium hydrogen carbonate, diazabicyclooctane (DABCO), diazabicyclononene (DBN), diazabicycloundecene (CBU), imidazole, 1-methylimidazole, 1,2-dimethylimidazole, titanium tetrabutoxide, titanium tetraisopropoxide, dibutyltin oxide, dibutyltin dilaurate, tin dioctoate, zirconium acetylacetonate, or mixtures of any two or more thereof.

* * * * *